United States Patent [19]

Isoda et al.

[11] Patent Number: 4,652,646

[45] Date of Patent: Mar. 24, 1987

[54] THIAZOLO[3,2-A][1,2,3]TRIAZOLO[4,5-D]PYRIMIDINE AND [1,3,4]THIADIAZOLO[3,2-A][1,2,3]TRIAZOLO[4,5-D]PYRIMIDINE DERIVATIVES

[75] Inventors: Sumiro Isoda; Norio Suzuki; Tamotsu Miwa; Shunzo Aibara, all of Tokyo, Japan

[73] Assignee: Daiichi Seiyaku Co., Ltd., Tokyo, Japan

[21] Appl. No.: 727,044

[22] Filed: Apr. 25, 1985

[30] Foreign Application Priority Data

Apr. 25, 1984 [JP] Japan .................................. 59-83232

[51] Int. Cl.$^4$ ............................................ C07D 513/14
[52] U.S. Cl. .................................. 544/251; 540/575; 544/104; 544/115
[58] Field of Search ...................... 544/251, 104, 115; 514/267; 540/575

[56] References Cited

U.S. PATENT DOCUMENTS 4,223,031  9/1980  Covington et al. .................. 514/267
4,366,156  12/1982  Temple, Jr. .......................... 514/267

Primary Examiner—Donald G. Daus
Assistant Examiner—Diana G. Rivers
Attorney, Agent, or Firm—Sughrue, Mion, Zinn, Macpeak and Seas

[57] ABSTRACT

Novel triazolopyrimidine compounds represented by the formula (I) and physiologically acceptable salts thereof are disclosed. These compounds have an excellent anti-allergic activity in oral administration and are useful for treatment and prophylaxis of allergic diseases such as bronchial asthma, allergic gastro-intestinal disorders, allergic rhinitis, hay fever, urticaria and the like.

8 Claims, No Drawings

THIAZOLO[3,2-A][1,2,3]TRIAZOLO[4,5-D]PYRIMIDINE AND [1,3,4]THIADIAZOLO[3,2-A][1,2,3]TRIAZOLO[4,5-D]PYRIMIDINE DERIVATIVES

FIELD OF THE INVENTION

This invention relates to triazolopyrimidine derivatives and physiologically acceptable salts thereof which are useful as anti-allergic agent.

BACKGROUND OF THE INVENTION

It is well known that a chemical mediator released by antigen-antibody reaction, e.g., histamine, plays an important role in inducing allergy. Typical known agents having an inhibitory activity on release of chemical mediators include sodium cromoglycate as disclosed in British Pat. No. 1,144,906. This compound, however, is not effective in oral administration and is generally administered by inhalation or by other topical applications as an aqueous solution thereof. Apparently, the inhalation has difficulty in administering the compound to infants or children and, moreover, can not be administered to patients sensitive to irritation caused by powder, and the topical application of aqueous solution is limited only to nasal cavity. Thus, development of excellent anti-allergic agents which can be administered orally has long been desired.

As a result of extensive studies on compounds having an anti-allergic activity, the present inventors found that the triazolopyrimidine derivatives of the present invention represented by the formula (I) below exhibit an excellent anti-allergic activity.

The condensed ring included in the compounds of this invention, i.e., thiazolo[3,2-a][1,2,3]triazolo[4,5-d]pyrimidine and [1,3,4]thiadiazolo[3,2-a][1,2,3]triazolo[4,5-d]pyrimidine, are novel condensed ring which have been first synthesized by the present inventors, and the compounds represented by the formula (I) having various substituents thereon are novel compounds.

The compounds represented by the formula (I) of this invention have the following characteristics:

(a) These compounds exhibit an inhibitory activity on release of chemical mediators induced by the antigen-antibody reaction, not only release of histamine which has been well known as a chemical mediator, but also release of a so-called "slow reacting substance of anaphylaxis" (SRS-A) which has recently been known to play an important role as a chemical mediator in the attack of asthma.

(b) These compounds exhibit such inhibitory activity in oral administration.

SUMMARY OF THE INVENTION

An object of this invention is therefore to provide a novel type of compounds having an anti-allergic activity.

Another object of the present invention is to provide a novel type of compounds which are useful for treatment and prophylaxis of allergic diseases such as bronchial asthma, allergic gastro-intestinal disorders, allergic rhinitis, hay fever, urticaria and the like.

DETAILED DESCRIPTION OF THE INVENTION

The triazolopyrimidine compounds according to the present invention are represented by the formula (I)

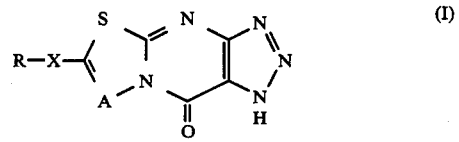

wherein:
A represents CH or N;
R represents an aryl group or a heterocyclic group, each of which may be substituted with one or more substituents selected from the group consisting of an alkyl group having 1 to 6 carbon atoms, an alkylene group having 1 to 10 carbon atoms, a cycloalkyl group having 3 to 10 carbon atoms, an alkoxy group having 1 to 6 carbon atoms, an alkylenedioxy group having 1 to 8 carbon atoms and a halogen atom; and
X represents a single bond, an alkylene group having 1 to 10 carbon atoms or an alkenylene group having 2 to 10 carbon atoms, each of which may be bonded to the substituent R or the condensed ring via an oxygen atom or a sulfur atom and may be substituted with one or more substituents selected from the group consisting of an alkyl group having 1 to 6 carbon atoms, an aryl group and a heterocyclic group;
and physiologically acceptable salts thereof.

Examples of alkyl group include methyl, ethyl, n-propyl, isopropyl, n-butyl, tert-butyl groups and the like.

Examples of aryl group include phenyl, biphenyl, naphthyl groups and the like.

Examples of heterocyclic group include furyl, thienyl, pyridyl, isochromanyl, chromanyl, chromenyl, benzodioxanyl, thiazolyl, isothiazolyl, thiadiazolyl, imidazolyl, pyrazolyl, triazolyl, pyrimidinyl, morpholinyl, pyrazinyl, pyridazinyl, pyrrolidinyl, piperidinyl, piperazinyl, homopiperazinyl, pyrrolyl, pyrrolinyl, imidazolyl, imidazolidinyl, oxazolinyl, oxazolidinyl, tetrazolyl, thiazolidinyl, indolyl, quinolyl, naphthyridinyl, quinazolinyl, pteridinyl, isobenzofuranyl, carbazolyl, acridinyl, xanthenyl, phenoxazinyl, perimidinyl group and the like.

The term "alkylene group" as used herein means a methylene or polymethylene group which may be substituted with one or more alkyl groups, and examples thereof include methylene, ethylene, trimethylene, heptamethylene, decamethylene, propylene, butylene, amylene, hexylene groups and the like.

Examples of cycloalkyl group include cyclopropyl, cyclobutyl, cyclopentyl, cyclohexyl, cycloheptyl groups and the like, which may be substituted with one or more alkyl groups, and the like.

The term "alkenylene group" as used herein means a group formed by removing two hydrogen atoms from alkene, and examples thereof include vinylene, propenylene, butenylene, 1-pentenylene, 2-pentenylene, 2-methyl-1-butenylene, 2-methyl-2-butenylene, 1-hexenylene, 2,3-dimethyl-2-butenylene groups and the like.

Of the compounds according to the present invention, compounds of the formula (I) wherein X represents an alkylene group and R represents a phenyl group which may be substituted with one or more substituents selected from the group consisting of an alkyl group, an alkoxy group and a halogen atom are preferred from the standpoint of their anti-allergic activity. Most preferred compounds are those of the formula (I) wherein X represents an ethylene group and R represents a phenyl group, a halophenyl group or an alkylphenyl group.

Although the compounds of the formula (I) are represented as their 1H-9-oxo compounds for the sake of convenience, it is to be understood that these compounds have the following tautomers (I'), (I'') and (I'''), which are within the scope of this invention.

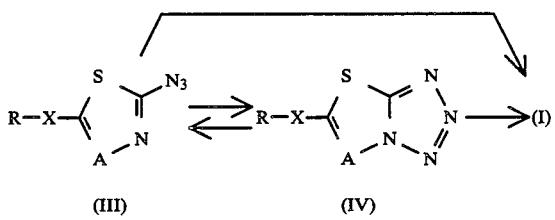

wherein A, R and X are as defined above. In this process, the compound of the formula (I) can be prepared

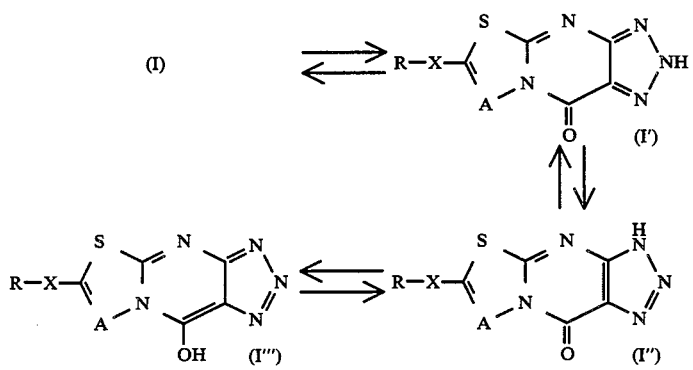

The compounds of the formula (I) can be prepared according to the following reaction scheme:

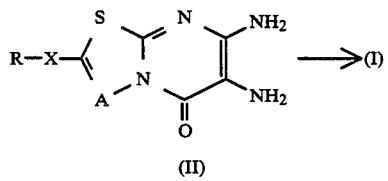

wherein A, R and X are as defined above.

The compound of the formula (I) can be prepared by diazotizing a compound of the formula (II) or a salt thereof with a nitrite in an acid. Examples of the acid include inorganic acids such as hydrochloric acid, hydrobromic acid and the like, organic acids such as acetic acid, propionic acid and the like, and a mixture thereof. Examples of the nitrite include sodium nitrite, potassium nitrite, etc. In the diazotizing reaction, the nitrite is used in at least an equimolar amount to the compound of the formula (II), and the acid is usually used in a large excess amount to the compound of the formula (II). The reaction can be generally carried out under ice-cooling or at a temperature up to room temperature (about 1° to 30° C.) for a period of from about 30 minutes to about 10 hours.

Alternatively, the above diazotization can be carried out by reacting a compound of the formula (II) with a nitrous acid ester such as isoamyl nitrite, tert-butyl nitrite, etc. in a solvent such as dimethylformamide, etc.

The compounds of the formula (I) can also be prepared according to the following reaction scheme:

by reacting a compound of the formula (III) or a tautomer thereof represented by the formula (IV) or a mixture thereof with a cyanoacetic acid ester such as methyl cyanoacetate, ethyl cyanoacetate and the like, in a solvent such as methanol, ethanol, etc. in the presence of an alkali such as sodium alkoxide, i.e., sodium methoxide or sodium ethoxide. The reaction can be carried out at a temperature in the range of from room temperature to a boiling point of the solvent used for a period of from about 30 minutes to about 10 hours.

The starting materials of the formulae (II), (III) and (IV) used in the above-described processes are novel compounds and can be prepared by the following processes:

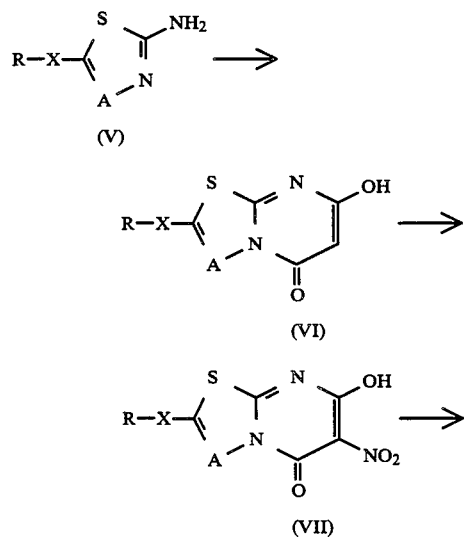

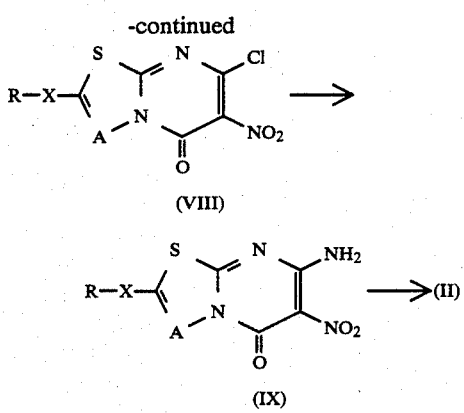

wherein A, R and X are as defined above.

Some of the compounds represented by the formula (V) are also novel compounds which can be prepared according to a known procedure for preparing thiadiazole derivatives as disclosed in, for example, Japanese Patent Application (OPI) No. 177997/83 (the term "OPI" as used herein means an unexamined published patent application) or a known procedure for preparing thiazole derivatives as disclosed in, for example, Ya. G. Bálon, M. D. Shul'man, N. V. Kuznetsov; Zh. Org. Khim., Vol. 15, No. 11, p2351, 1979.

The above processes for preparing the starting materials are hereinafter described in detail.

The compound of the formula (VI) can be prepared by reacting a compound of the formula (V) with a malonic acid ester, preferably 2,4,6-trichlorophenyl malonate, in the presence or absence of an inert solvent, for example, Dowtherm A, etc. The reaction can be carried out at a temperature of from about 100° to about 250° C. for a period of from about 30 minutes to about 10 hours.

The compound of the formula (VII) can be prepared by reacting the compound of the formula (VI) with fuming nitric acid in the presence or absence of an inert solvent, for example, acetic acid, diethyl ether, etc. The reaction can be carried out under ice cooling or at a temperature up to about 80° C. for a period of from about 30 minutes to about 15 hours.

The compound of the formula (VIII) can be prepared by reacting the compound of the formula (VII) with phosphorus oxychloride in the presence of an acid acceptor and in the presence or absence of a solvent. Preferred acid acceptors include an organic base such as dimethylaniline, diethylaniline, tripropylamine, etc. The reaction can be carried out at a temperature of from room temperature to about 100° C. for a period of from about 30 minutes to about 5 hours.

The compound of the formula (IX) can be prepared by reacting the compound of the formula (VIII) with ammonia in the presence or absence of a solvent, for example, an alcohol, dimethylformamide, dioxane and the like. The reaction can be carried out under ice cooling or at a temperature up to about 80° C. for a period of from about 30 minutes to about 5 hours.

The starting compound of the formula (II) can be prepared by subjecting the compound of the formula (IX) to a usual reduction reaction, for example, catalytic reduction using palladium or reduction using a metal and an acid such as tin and hydrochloric acid.

The starting materials of the formulae (III) and (IV) which exist as tautomers can be prepared by reacting the compound of the formula (V) with an alkali and p-toluenesulfonyl azide in the presence or absence of a solvent such as dichloromethane.

Examples of salts of the compounds represented by the formula (I) include alkali metal salts such as sodium and potassium salts, alkaline earth metal salts such as calcium salt, and amine salts such as ammonium, tris(hydroxymethyl)aminomethane and N-methylglucamine salts, and the like.

The excellent anti-allergic activity of the compounds of this invention has been confirmed by evaluating an inhibitory activity on release of histamine and SRS-A induced by passive peritoneal anaphylaxis (PPA) reaction in rat as well as an inhibitory activity on passive cutaneous anaphylaxis (PCA) reaction in rats. As a result of these tests, it has been found that the compounds of this invention inhibit not only the release of histamine but also the release of SRS-A to a significant degree in the PPA reaction, and also inhibit the PCA reaction to a significant degree in oral administration of the compounds. Thus, the compounds of this invention have been found to possess a strong anti-allergic activity and, therefore, are useful as anti-allergic agent in oral administration.

In contrast, sodium cromoglycate which has been known as an anti-allergic agent having an inhibitory activity on release of chemical mediators did not inhibit the release of SRS-A in the PPA reaction and also did not inhibit the PCA reaction in oral administration.

These anti-allergic activities are described in more detail in Test Examples hereinafter described.

The compounds of the formula (I) and the salts thereof can be generally administered orally at a dose level of from about 150 mg to about 600 mg, 2 to 3 times per day for adult human, in a form of pharmaceutical preparation such as tablets, capsules, syrups and the like.

The compounds of the formula (I) are relatively of low toxicity, and $LD_{50}$ values determined in rats by oral administration are higher than 2 g/kg for the compounds of Examples 1, 9, 17, 18, 20, 21, 23, 42, 47, 48, 49, 50, 53, 54 and 55.

The present invention is further described in more detail by the following Examples, Reference Examples and Test Examples, but the present invention is not limited thereto.

EXAMPLE 1

6-(4-tert-Butylphenyl)-[1,3,4]thiadiazolo[3,2-a][1,2,3]triazolo[4,5-d]pyrimidin-9(1H)-one 1.0 of 6,7-diamino-2-(4-tert-butylphenyl)-5H-[1,3,4]thiadiazolo[3,2-a]pyrimidin-5-one was suspended in a mixture of 20 ml of concentrated hydrochloric acid and 20 ml of water, and 2 ml of an aqueous solution containing 0.70 g of sodium nitrite was added dropwise thereto while cooling below 5° C. and stirring. The mixture was stirred at that temperature for 1.5 hours and then diluted with water. The resulting precipitate was filtered and recrystallized from chloroform-ethanol to obtain 0.88 g of the titled compound as pale yellow prisms. Melting Point: 293°-296° C. (decomposition).

In the same manner as described in Example 1, each of the following compounds represented by the formula (I) of Examples 2 to 8 was prepared.

| Example No. | A | R—X— | Melting point (°C.) |
|---|---|---|---|
| 2 | N | 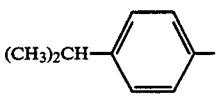 (CH₃)₂CH— | 269–271 |
| 3 | N | 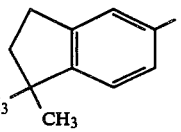 CH₃O— | 285–287 |
| 4 | N | 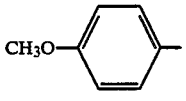 | >300 |
| 5 | CH | 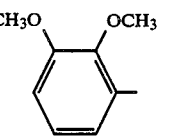 (CH₃)₂CH— | 305–307 |
| 6 | CH | 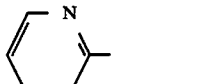 (CH₃)₃C— | >300 |
| 7 | CH | 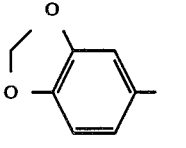 | >300 |
| 8 | CH | 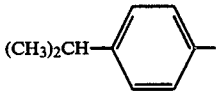 | >300 |

EXAMPLE 9

6-(2-Phenylethyl)-[1,3,4]thiadiazolo[3,2-a][1,2,3]triazolo[4,5-d]pyrimidin-9(1H)-one 10.7 g of 7-amino-6-nitro-2-(2-phenylethyl)-5H-[1,3,4]thiadiazolo[3,2-a]pyrimidin-5-one was suspended in 130 ml of dioxane, and 18 g of tin powder was added thereto. Then, 22 ml of concentrated hydrochloric acid was added dropwise to the gentle refluxing suspension. The gentle refluxing was further continued and, after confirming disappearance of the starting material, any insoluble material was removed by filtration. The filtrate was concentrated, and the precipitate was separated by filtration and suspended in 300 ml of concentrated hydrochloric acid-water (1:1 by volume). 20 ml of an aqueous solution containing 6.2 g of sodium nitrite was then added dropwise to the suspension at a temperature below 5° C. and, after stirring the mixture at 5° C. for 3 hours, the precipitate was separated by filtration. After washing with water and drying, the precipitate was recrystallized from chloroform-ethanol to obtain 5.3 g of the titled compound. Melting point: 295°–296° C.

In the same manner as described in Example 9, each of the following compounds represented by the formula (I) of Examples 10 to 79 was prepared.

| Example No. | A | R—X— | Melting Point (°C.) |
|---|---|---|---|
| 10 | N | 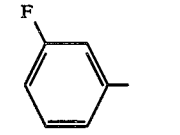 | >300 |
| 11 | N | 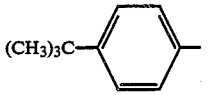 CH₃O, OCH₃ | 276–278 |
| 12 | N | 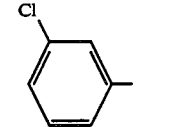 | >300 |
| 13 | N | 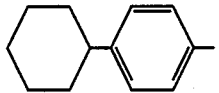 F | 296–298 |
| 14 | N | 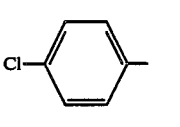 Cl | 290–292 |
| 15 | N | 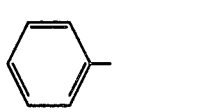 Cl— | 296–299 |
| 16 | N | 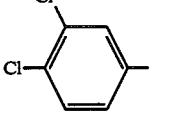 Cl, Cl | >300 |
| 17 | N | 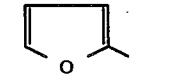 | >300 |
| 18 | N | 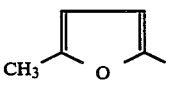 CH₃ | >300 |
| 19 | N | 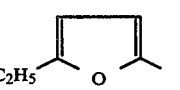 C₂H₅ | >300 |
| 20 | N | 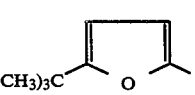 (CH₃)₃C | >300 |
| 21 | N | 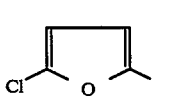 Cl | >300 |

-continued
| Example No. | A | R—X— | Melting Point (°C.) |
|---|---|---|---|
| 22 | N | 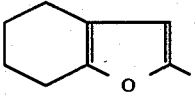 | >300 |
| 23 | N | 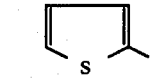 | >300 |
| 24 | N | 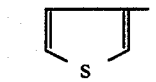 | >300 |
| 25 | N | 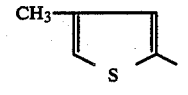 | 280–283 |
| 26 | N | 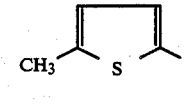 | 295–297 |
| 27 | N | 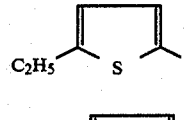 | >300 |
| 28 | N | 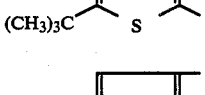 | 253–256 |
| 29 | N | 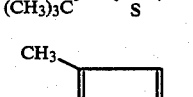 | 225–230 |
| 30 | N | 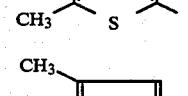 | >300 |
| 31 | N | 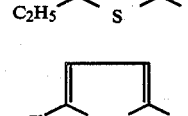 | 270–273 |
| 32 | N |  | >300 |
| 33 | N | 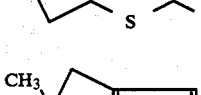 | >300 |
| 34 | N | 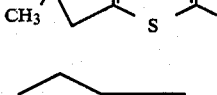 | >300 |
| 35 | N | 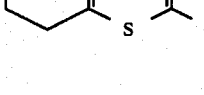 | >300 |
-continued
| Example No. | A | R—X— | Melting Point (°C.) |
|---|---|---|---|
| 36 | N | 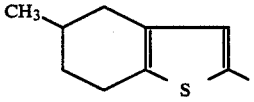 | 298–303 |
| 37 | N | 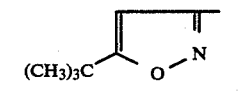 | 297–300 |
| 38 | N | 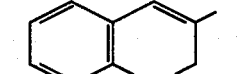 | >300 |
| 39 | N | 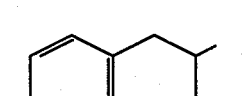 | >300 |
| 40 | N | 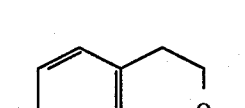 | 260–280 (not clear) |
| 41 | N | 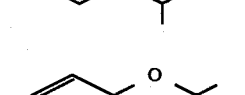 | >300 |
| 42 | N | 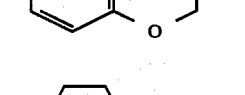 | >300 |
| 43 | N | 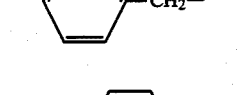 | 267 (decomposition) (not clear) |
| 44 | N | 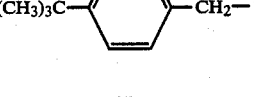 | >300 |
| 45 | N | 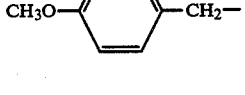 | 285–288 |
| 46 | N | 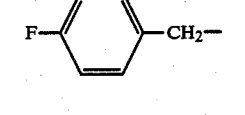 | >300 |
| 47 | N | 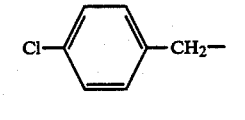 | >300 |

-continued

| Example No. | A | R—X— | Melting Point (°C.) |
|---|---|---|---|
| 48 | N | 2-CH₃-C₆H₄-(CH₂)₂— | 277–279 |
| 49 | N | 3-CH₃-C₆H₄-(CH₂)₂— | 276–278 |
| 50 | N | 4-CH₃-C₆H₄-(CH₂)₂— | 284–285 |
| 51 | N | 3-CH₃O-C₆H₄-(CH₂)₂— | 285–287 |
| 52 | N | 4-CH₃O-C₆H₄-(CH₂)₂— | 270–272 |
| 53 | N | 4-F-C₆H₄-(CH₂)₂— | 284–286 |
| 54 | N | 3-Cl-C₆H₄-(CH₂)₂— | 277–279 |
| 55 | N | 4-Cl-C₆H₄-(CH₂)₂— | 290–292 |
| 56 | N | 3,4-Cl₂-C₆H₃-(CH₂)₂— | 295–297 |
| 57 | N | (C₆H₅)₂CH—CH₂— | 265–267 |
| 58 | N | C₆H₅—CH(CH₃)—CH₂— | 276–278 |
| 59 | N | C₆H₅—C(CH₃)₂—CH₂— | 297–302 |
| 60 | N | C₆H₅—(CH₂)₃— | 265–267 |
| 61 | N | C₆H₅—(CH₂)₄— | 279–281 |
| 62 | N | C₆H₅—CH=CH— | >300 |
| 63 | N | (C₆H₅)₂C=CH— | >300 |
| 64 | N | C₆H₅—OCH₂— | >300 |
| 65 | N | 4-(CH₃)₃C-C₆H₄-OCH₂— | >300 |
| 66 | N | 4-F-C₆H₄-OCH₂— | 283–285 |
| 67 | N | 4-Cl-C₆H₄-OCH₂— | >300 |
| 68 | N | 6-(5,6,7,8-tetrahydronaphthyl)-OCH₂— | >300 |
| 69 | N | 4-(CH₃)₃C-C₆H₄-O(CH₂)₂— | 245–248 (decomposition) |
| 70 | N | C₆H₅—SCH₂— | 249–251 |

-continued

| Example No. | A | R—X— | Melting Point (°C.) |
|---|---|---|---|
| 71 | N |  (CH₃)₃C—⟨phenyl⟩—SCH₂— | 288-290 |
| 72 | N | 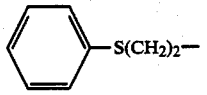 ⟨phenyl⟩—S(CH₂)₂— | 228-230 |
| 73 | CH | 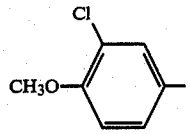 2-Cl, 4-CH₃O-phenyl— | 270-275 |
| 74 | CH | 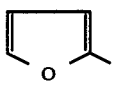 furan-2-yl— | >300 |
| 75 | CH | 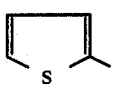 thiophen-2-yl— | >300 |
| 76 | CH | 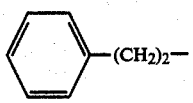 ⟨phenyl⟩—(CH₂)₂— | 250-253 (decomposition) |
| 77 | CH | 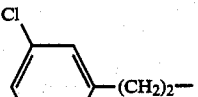 Cl-⟨phenyl⟩—(CH₂)₂— | 232-233 (decomposition) |
| 78 | N | 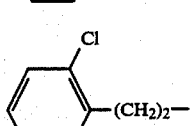 Cl-⟨phenyl⟩—(CH₂)₂— | 273-276 |
| 79 | N | 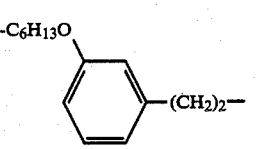 n-C₆H₁₃O-⟨phenyl⟩—(CH₂)₂— | 212-214 |

EXAMPLE 80

6-(4-Methylphenyl)-[1,3,4]thiadiazolo[3,2-a][1,2,3]triazolo[4,5-d]pyrimidin-9(1H)-one monohydrate 3.12 g of ethyl cyanoacetate was added to 15 ml of an ethanol solution containing 1.88 g of sodium ethoxide and, after stirring, 3.0 g of 2-azido-5-(4-methylphenyl)-1,3,4-thiadiazole was added to the solution. The mixture was stirred at room temperature for 20 minutes and then gently refluxed for 2 hours. After allowing to cool, the precipitate was separated by filtration, washed with ethanol and added to dilute hydrochloric acid. The resulting precipitate was separated by filtration and washed with water to obtain 2.54 g of the titled compound as a colorless powder. Melting Point: higher than 300° C.

In the same manner as described in Example 80, each of the following compounds represented by the formula (I) of Examples 81 to 84 was prepared.

| Example No. | A | R—X— | Melting Point (°C.) |
|---|---|---|---|
| 81 | N | 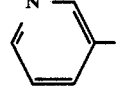 pyridyl— | >300 |
| 82 | N | 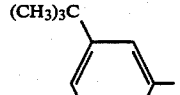 (CH₃)₃C-⟨phenyl⟩— | 250-253 |
| 83 | N | 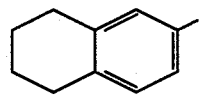 tetrahydronaphthyl— | 284-287 |
| 84 | CH | 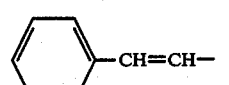 ⟨phenyl⟩—CH=CH— | >300 |

EXAMPLE 85

6-(4-tert-Butylphenyl)-[1,3,4]thiadiazolo[3,2-a][1,2,3]triazolo[4,5-d]pyrimidin-9(1H)-one tris(hydroxymethyl)aminomethane salt.

A mixture of 0.80 g of the product obtained in Example 1 and 0.296 g of tris(hydroxymethyl)aminomethane was heated in ethanol. After allowing the mixture to cool, the resulting precipitate was separated by filtration to obtain 0.861 g of the titled compound. Melting Point: 160°-165° C. (not clear).

EXAMPLE 86

6-(4-Methoxyphenyl)-[1,3,4]thiadiazolo[3,2-a][1,2,3]triazolo[4,5-d]pyrimidin-9(1H)-one tris(hydroxymethyl)aminomethane salt.

In the same manner as described in Example 85, the titled compound was prepared from the product obtained in Example 3 and tris(hydroxymethyl)aminomethane. Melting Point: 160°-165° C. (not clear).

EXAMPLE 87

6-(2-Phenylethyl)-[1,3,4]thiadiazolo[3,2-a][1,2,3]triazolo[4,5-d]pyrimidin-9(1H)-one sodium salt monohydrate 22.35 g of the product obtained in Example 9 was suspended in 300 ml of water, and 79 ml of a 1N aqueous solution of sodium hydroxide was added to the suspension, followed by stirring for 1 hour. Any insoluble material was separated by filtration, and the filtrate was concentrated under reduced pressure to a volume of about 100 ml. 500 ml of isopropanol was added to the concentrate and, after allowing the mixture to stand under ice-cooling, the precipitate formed was separated by filtration, washed with isopropanol and dried under reduced pressure at 80° C. for 4 hours to obtain 19.4 g of the titled compound as a pale yellow substance. Melting Point: higher than 300° C. (with loss of water of crystallization at about 150° C.).

NMR (δ in D₂O): 2.6–3.3 (4H, m), 6.90 (5H, s).

EXAMPLE 88

6-(2-Phenylethyl)-[1,3,4]thiadiazolo[3,2-a][1,2,3]triazolo[4,5-d]pyrimidin-9(1H)-one potassium salt sesquihydrate The titled compound was obtained in the same manner as described in Example 87 using the product obtained in Example 9 and a 1N aqueous solution of potassium hydroxide, but air-drying the product for 3 days. Melting Point: higher than 300° C. (with loss of water of crystallization at about 90° C.).

NMR (δ in D₂O): 2.6–3.3 (4H, m), 6.90 (5H, s).

EXAMPLE 89

6-(2-Phenylethyl)-[1,3,4[thiadiazolo[3,2-a][1,2,3]triazolo[4,5-]pyrimidin-9(1H)-one lithium salt dihydrate The titled compound was obtained in the same manner as described in Example 87 using the product obtained in Example 9 and a 1N aqueous solution of lithium hydroxide, but air-drying the product for 3 days. Melting Point: 247°–255° C. (decomposition and with loss of water of crystallization at about 150° C.).

NMR (δ in D₂O): 2.6–3.3 (4H, m), 6.90 (5H, s).

Syntheses of the starting materials of the formulae (II), (III), (IV) and (IX) used in the above Examples are described in the following Reference Examples. In these Reference Examples, the substituents A, R and X of the starting materials are identical to those in the compounds of the formula (I) of Examples having the corresponding number.

SYNTHESIS OF STARTING COMPOUND OF FORMULA (II)

REFERENCE EXAMPLE 1

6,7-Diamino-2-(4-tert-butylphenyl)-5H-[1,3,4]thiadiazolo[3,2-a]pyrimidin-5-one (i) A mixture of 9.3 g of 2-amino-5-(4-tert-butylphenyl)-1,3,4-thiadiazole, 20 g of 2,4,6-trichlorophenyl malonate and 50 ml of Dowtherm A was heated at a temperature of 120° to 130° C. for 2 hours. After allowing the mixture to cool, the precipitate was separated by filtration, washed successively with isopropanol and diethyl ether to obtain 11.6 g of 2-(4-tert-butylphenyl)-7-hydroxy-5H-[1,3,4]thiadiazolo[3,2-a]pyrimidin-5-one as a colorless, crystalline powder having a melting point of 265° to 268° C. (decomposition).

Elemental Analysis for $C_{15}H_{15}N_3O_2S$: Calc'd: C: 59.78; H: 5.02; N: 13.94. Found: C: 60.19; H: 5.34; N: 13.62.

(ii) 10.0 g of 2-(4-tert-butylphenyl)-7-hydroxy-5H-[1,3,4]thiadiazolo[3,2-a]pyrimidin-5-one was suspended in 100 ml of acetic acid, and 15 ml of fuming nitric acid was added dropwise to the suspension while maintaining the temperature at 80° C. After completion of the reaction, the mixture was cooled and the precipitate was separated by filtration to obtain 7.1 g of 2-(4-tert-butylphenyl)-7-hydroxy-6-nitro-5H-[1,3,4]thiadiazolo[3,2-a]pyrimidin-5-one as pale yellow prisms having a melting point of 245° to 246° C. (decomposition).

Elemental Analysis for $C_{15}H_{14}N_4O_4S$: Calc'd: C: 52.01; H: 4.07; N: 16.18. Found: C: 52.08; H: 4.43; N: 16.18.

(iii) 6.0 g of 2-(4-tert-butylphenyl)-7-hydroxy-6-nitro-5H-[1,3,4]thiadiazolo[3,2-a]pyrimidin-5-one was added to a mixture of 25 ml of phosphorus oxychloride and 4 ml of diethylaniline, and the resulting mixture was heated at a temperature of 70° to 80° C. for 2 hours. After cooling, the precipitate formed was filtered, washed successively with water, isopropanol and diethyl ether to obtain 4.3 g of 2-(4-tert-butylphenyl)-7-chloro-6-nitro-5H-[1,3,4]thiadiazolo[3,2-a]pyrimidin-5-one as crystals having a melting point of 245° to 248° C.

Elemental Analysis for $C_{15}H_{13}ClN_4O_3S$: Calc'd: C: 49.38; H: 3.32; N: 15.36. Found: C: 49.02; H: 3.27; N: 15.48.

(iv) 1.9 g of 2-(4-tert-butylphenyl)-7-chloro-6-nitro-5H-[1,3,4]thiadiazolo[3,2-a]pyrimidin-5-one was suspended in a mixture of 20 ml of ethanol and 10 ml of dimethylformamide, and 5 ml of concentrated aqueous ammonia was added dropwise to the suspension while maintaining at a temperature of 60° C. to 70° C. After heating at that temperature for 2 hours, the mixture was cooled and the precipitate formed was separated by filtration to obtain 1.3 g of 7-amino-2-(4-tert-butylphenyl)-6-nitro-5H-[1,3,4]thiadiazolo[3,2-a]pyrimidin-5-one as pale yellow prisms having a melting point higher than 300° C.

Elemental Analysis for $C_{15}H_{15}N_5O_3S$: Calc'd: C: 52.16; H: 4.38; N: 20.28. Found: C: 51.23; H: 4.62; N: 20.37.

(v) 2.75 g of 7-amino-2-(4-tert-butylphenyl)-6-nitro-5H-[1,3,4] thiadiazolo[3,2-a]pyrimidin-5-one was dissolved in 200 ml of warmed dimethylformamide, and 20 ml of acetic acid and 2.0 g of 5% palladium-carbon were added to the solution. Catalytic reduction was carried out at a temperature of 40° to 60° C. After the calculated amount of hydrogen was absorbed, the catalyst was removed by filtration while hot, and the filtrate was concentrated under reduced pressure. The precipitate formed was separated by filtration to obtain 2.0 g of 6,7-diamino-2-(4-tert-butylphenyl)-5H-[1,3,4]thiadiazolo[3,2-a]pyrimidin-5-one as yellow needles.

Elemental Analysis for $C_{15}H_{17}N_5OS$: Calc'd: C: 57.12; H: 5.43; N: 22.21. Found: C: 57.06; H: 5.33; N: 22.21.

In the same manner as described in Reference Example 1, each of the compounds represented by the formula (II) of Reference Examples 2 to 7 was prepared. In these compounds of the formula (II), the substituents A, R and X are the same as those of Examples 2 to 7, respectively.

| Compound of Reference Example | Melting Point (°C.) |
|---|---|
| 2 | 279–282 |
| 3 | >300 |
| 4 | 293–296 (decomposition) |
| 5 | 255–258 |
| 6 | 270–275 |
| 7 | 265–275 |

REFERENCE EXAMPLE 8

6,7-Diamino-2-phenyl-5H-thiazolo[3,2-a]pyrimidin-5-one (i) In the same manner as described in steps (i), (ii), (iii) and (iv) of Reference Example 1, 7-amino-6-nitro-2-phenyl-5H-thiazolo[3,2-a]pyrimidin-5-one having a melting point of 291°–294° C. was obtained.

(ii) 2.0 g of 7-amino-6-nitro-2-phenyl-5H-thiazolo[3,2-a]pyrimidin-5-one was suspended in 50 ml of 90% dioxane, and 3.0 g of tin powder and 5 ml of concentrated hydrochloric acid were added thereto, followed by stirring the mixture at 80° to 90° C. for 30 minutes. Any insoluble material was removed by filtration, and the filtrate was concentrated. After cooling, the precipitate formed was separated by filtration and added to concentrated aqueous ammonia. The precipitate was separated by filtration and recrystallized from dimethylformamide to obtain 6,7-diamino-2-phenyl-5H-thiazolo[3,2-a]pyrimidin-5-one as yellow needles having a melting point higher than 300° C.

Elemental Analysis for $C_{12}H_{10}N_4OS$: Calc'd: C: 55.80; H: 3.90; N: 21.69. Found: C: 56.01; H: 4.09; N: 21.60.

In the same manner as described in steps (i), (ii), (iii) and (iv) of Reference Example 1, each of the compounds represented by the formula (IX) of Reference Examples 9 to 79 was obtained. In these compounds, the substituents A, R and X are the same as those of Examples 9 to 79, respectively.

| Compound of Reference Example | Melting Point (°C.) |
| --- | --- |
| 9 | 268–270 |
| 10 | >300 |
| 11 | 279–285 |
| 12 | >300 |
| 13 | >300 |
| 14 | >300 |
| 15 | >295 |
| 16 | 280–286 |
| 17 | >300 |
| 18 | >280 (not clear) |
| 19 | 282–284 |
| 20 | >300 |
| 21 | >300 |
| 22 | >290 (not clear) |
| 23 | >300 |
| 24 | >300 |
| 25 | 292–296 |
| 26 | >300 |
| 27 | >300 |
| 28 | 272–275 |
| 29 | 281–284 |
| 30 | >300 |
| 31 | >300 |
| 32 | >300 |
| 33 | >300 |
| 34 | >300 |
| 35 | >300 |
| 36 | >300 |
| 37 | 240–248 |
| 38 | >300 |
| 39 | >300 |
| 40 | >300 |
| 41 | >300 |
| 42 | 286–289 |
| 43 | 258–261 |
| 44 | 298–300 |
| 45 | 285–287 |
| 46 | 286–287 |
| 47 | >300 |
| 48 | 264–268 |
| 49 | 262–264 |
| 50 | 273–274 |
| 51 | 264–267 |
| 52 | 254–257 |
| 53 | 260–264 |
| 54 | 248–249 |
| 55 | 248–250 |
| 56 | 272–273 |
| 57 | 220–222 |
| 58 | 252–260 (decomposition) |
| 59 | >300 |
| 60 | 252–255 |
| 61 | 249–252 |
| 62 | >300 |
| 63 | 287–290 |
| 64 | 267–268 |
| 65 | 274 (decomposition) |
| 66 | 249–251 |
| 67 | >300 |
| 68 | 269–271 |
| 69 | 243 (decomposition) |
| 70 | 150–155 |
| 71 | 200–202 |
| 72 | 234–237 |
| 73 | >300 |
| 74 | 280 (decomposition) |
| 75 | 290–297 |
| 76 | 218–223 |
| 77 | 215–218 |
| 78 | 235–243 |
| 79 | 180–187 (not clear) |

REFERENCE EXAMPLE 80

2-Azido-5-(4-methylphenyl)-1,2,4-thiadiazole

A mixture of 3.67 g of 2-amino-5-(4-methylphenyl)-1,3,4-thiadiazole, 3.89 g of p-toluenesulfonyl azide, 0.68 g of tetrabutylammonium hydrogensulfate, 40 ml of a 40% aqueous sodium hydroxide solution and 60 ml of dichloromethane was vigorously stirred at room temperature. After 2 hours, cold water and dichloromethane were added to the mixture, and any insoluble material was removed by filtration. The dichloromethane layer was washed with water, dried and dichloromethane was distilled off. The resulting residue was recrystallized from methanol to obtain 3.02 g of the titled compound as colorless crystals having a melting point of 129° to 130° C. (decomposition).

Elemental Analysis for $C_9H_7N_5S$: Calc'd: C: 49.76; H: 3.25; N: 32.24. Found: C: 49.96; H: 3.33; N: 32.51.

REFERENCE EXAMPLE 81

2-Azido-5-(3-pyridyl)-1,3,4-thiadiazole

The titled compound was obtained from 2-amino-5-(3-pyridyl)-1,3,4-thiadiazole in the same manner as described in Reference Example 80. Melting Point: 121°–123° C. (decomposition).

REFERENCE EXAMPLES 82 AND 83

In the same manner as described in Reference Example 80, each of the compounds represented by the formula (IV) of Reference Examples 82 and 83 was obtained.

| Compound of Reference Example | Melting Point (°C.) |
|---|---|
| 82 | 129–131 |
| 83 | 113–114 |

REFERENCE EXAMPLE 84

2-Azido-5-styrylthiazole

The titled compound was prepared from 2-amino-5-styrylthiazole in the same manner as described in Reference Example 80. Melting Point: 112°–130° C. (decomposition).

Some of the starting compounds having the formula (V) are novel compounds and their melting points are identified as follows. The substituents A, R and X in the following compounds are identical to those in the compounds of the formula (I) of Examples having the corresponding number.

| Starting Compound of Formula (V) | Melting point (°C.) |
|---|---|
| 2 | 215–217 |
| 5 | 175–180 |
| 6 | 198–200 |
| 7 | −270 (not clear, decomposition) |
| 10 | 220–222 |
| 18 | 237–239 |
| 19 | 195–199 |
| 20 | 273–278 |
| 22 | 241–243 |
| 25 | 221–225 |
| 27 | 206–209 |
| 28 | 203–205 |
| 29 | 235–239 |
| 30 | 237–238 |
| 31 | 195–197 |
| 32 | 207–209 |

-continued

| Starting Compound of Formula (V) | Melting point (°C.) |
|---|---|
| 33 | 255–260 |
| 34 | 251–253 |
| 35 | 250–253 |
| 36 | 265–270 |
| 37 | 213–215 |
| 38 | 263–267 |
| 39 | 224–226 |
| 40 | 172–174 |
| 41 | 230–233 |
| 43 | 223 |
| 48 | 193–194 |
| 49 | 173.5–174.5 |
| 50 | −214 (not clear) |
| 51 | 167–168 |
| 52 | 212–213 |
| 54 | 170–172 |
| 55 | 219–221 |
| 56 | 199–201 |
| 58 | −230 (not clear) |
| 59 | 192–194 |
| 65 | 219 |
| 67 | 220–223 |
| 68 | 205–207 |
| 69 | 222 |
| 71 | 167–169 |
| 73 | 198–206 |
| 74 | 81–82 |
| 75 | 153–156 |
| 76 | 135–137 |
| 77 | 110–111 |
| 78 | 196–198 |
| 79 | 164–165 |
| 83 | 181–188 |
| 84 | −254 (not clear) |

Elemental analysis and infrared absorption spectrum of the compounds of the formula (I) described in Examples are shown below.

| Compound of Example | Formula | Elemental Analysis % (calc'd)/(found) | | | IR Absorption Spectrum (KBr) cm$^{-1}$ | | | | |
|---|---|---|---|---|---|---|---|---|---|
| | | C | H | N | | | | | |
| 1 | $C_{15}H_{14}N_6OS$ | 55.20 | 4.32 | 25.75 | 3140 | 3060 | 2940 | 1735 | 1690 |
| | | 55.39 | 4.54 | 25.82 | 1550 | 1480 | 1430 | 1255 | 1190 |
| 2 | $C_{14}H_{12}N_6OS$ | 53.83 | 3.87 | 26.91 | 3050 | 2850 | 1720 | 1670 | 1550 |
| | | 54.27 | 4.08 | 26.93 | 1520 | 1490 | 1290 | 1255 | 1190 |
| 3 | $C_{12}H_8N_6O_2S$ | 45.69 | 3.83 | 25.66 | 3070 | 1695 | 1600 | 1530 | 1495 |
| | $C_3H_7NO \cdot H_2O$ | 45.40 | 3.56 | 25.59 | 1440 | 1310 | 1260 | 1175 | 835 |
| 4 | $C_{10}H_5N_7OS$ | 43.48 | 2.17 | 35.50 | 3080 | 1700 | 1565 | 1515 | 1470 |
| | $\frac{1}{2}H_2O$ | 43.88 | 2.25 | 34.97 | 1455 | 1430 | 1235 | 990 | 775 |
| 5 | $C_{15}H_{13}N_5OS$ | 57.86 | 4.21 | 22.50 | 3160 | 3100 | 2950 | 1690 | 1570 |
| | | 57.78 | 4.33 | 22.33 | 1520 | 1470 | 1240 | 1150 | 770 |
| 6 | $C_{16}H_{15}N_5OS$ | 58.25 | 4.74 | 21.23 | 3160 | 3100 | 2950 | 1685 | 1570 |
| | $\frac{1}{2}H_2O$ | 58.73 | 5.16 | 20.98 | 1525 | 1465 | 1240 | 1150 | 770 |
| 7 | $C_{18}H_{17}N_5OS$ | 60.74 | 4.95 | 19.67 | 3160 | 3100 | 2910 | 1685 | 1560 |
| | $\frac{1}{2}H_2O$ | 60.62 | 4.89 | 19.35 | 1520 | 1460 | 1240 | 1150 | 755 |
| 8 | $C_{12}H_7N_5OS$ | 53.01 | 3.46 | 25.19 | 3080 | 2920 | 2780 | 1710 | 1565 |
| | $\frac{1}{2}C_3H_7NO$ | 53.02 | 3.79 | 24.89 | 1510 | 1450 | 1395 | 1235 | 755 |
| 9 | $C_{13}H_{10}N_6OS$ | 52.34 | 3.38 | 28.17 | 3140 | 3080 | 1700 | 1565 | 1520 |
| | | 52.50 | 3.56 | 28.20 | 1470 | 1265 | 1000 | 970 | 770 |
| 10 | $C_{16}H_{14}N_6OS$ | 56.79 | 4.17 | 24.84 | 3130 | 3070 | 2940 | 1740 | 1700 |
| | | 56.51 | 4.31 | 24.65 | 1555 | 1530 | 1480 | 1420 | 1190 |
| 11 | $C_{13}H_{10}N_6O_3S$ | 47.27 | 3.05 | 25.44 | 1725 | 1635 | 1570 | 1530 | 1510 |
| | | 47.18 | 3.34 | 25.10 | 1470 | 1270 | 1235 | 1080 | 990 |
| 12 | $C_{12}H_6N_6O_3S$ | 46.51 | 3.38 | 25.31 | 3420 | 1730 | 1650 | 1560 | 1525 |
| | $C_3H_7NO$ | 46.23 | 3.30 | 25.22 | 1485 | 1445 | 1270 | 1245 | 1030 |
| 13 | $C_{11}H_5FN_6OS$ | 45.83 | 1.75 | 29.16 | 3060 | 1690 | 1580 | 1520 | 1470 |
| | | 46.29 | 2.24 | 28.90 | 1440 | 1250 | 895 | 800 | 760 |
| 14 | $C_{11}H_5ClN_6OS$ | 43.36 | 1.65 | 27.58 | 3400 | 3150 | 1710 | 1550 | 1525 |
| | | 43.85 | 1.94 | 27.15 | 1415 | 1240 | 1190 | 1170 | 670 |
| 15 | $C_{11}H_5ClN_6OS$ | 43.36 | 1.65 | 27.58 | 2830 | 1725 | 1680 | 1585 | 1550 |
| | | 43.47 | 1.95 | 27.65 | 1520 | 1475 | 1255 | 1190 | 1080 |
| 16 | $C_{11}H_4Cl_2N_6OS$ | 38.96 | 1.19 | 24.78 | 3060 | 2850 | 1725 | 1685 | 1550 |

-continued

| Compound of Example | Formula | Elemental Analysis % (calc'd)/(found) | | | IR Absorption Spectrum (KBr) cm$^{-1}$ | | | | |
|---|---|---|---|---|---|---|---|---|---|
| | | C | H | N | | | | | |
| | | 39.36 | 1.58 | 24.72 | 1520 | 1470 | 1195 | 990 | 965 |
| 17 | $C_9H_4N_6O_2S$ | 41.54 | 1.55 | 32.30 | 3100 | 1680 | 1565 | 1510 | 1470 |
| | | 41.69 | 1.92 | 32.05 | 1250 | 1225 | 870 | 780 | 750 |
| 18 | $C_{10}H_6N_6O_2S$ | 44.13 | 2.67 | 29.92 | 2980 | 2880 | 1690 | 1575 | 1530 |
| | ¼$C_3H_7NO$ | 44.12 | 2.76 | 29.98 | 1480 | 1260 | 1240 | 1010 | 895 |
| 19 | $C_{11}H_8N_6O_2S$ | 45.83 | 2.80 | 29.15 | 3080 | 1720 | 1640 | 1525 | 1470 |
| | | 45.97 | 2.99 | 28.71 | 1410 | 1370 | 1235 | 750 | 730 |
| 20 | $C_{13}H_{12}N_6O_2S$ | 49.98 | 3.87 | 26.91 | 3180 | 3080 | 1710 | 1565 | 1530 |
| | | 49.37 | 3.96 | 26.47 | 1510 | 1250 | 1000 | 890 | 800 |
| 21 | $C_9H_3ClN_6O_2S$ | 39.19 | 2.74 | 26.66 | 3090 | 1735 | 1665 | 1600 | 1545 |
| | $C_3H_7NO$ | 39.53 | 2.82 | 26.86 | 1510 | 1460 | 1200 | 1010 | 970 |
| 22 | $C_{13}H_{10}N_6O_2S$ | 49.67 | 3.21 | 26.74 | 3140 | 3090 | 2930 | 1705 | 1570 |
| | | 49.30 | 3.26 | 26.43 | 1545 | 1525 | 1155 | 1005 | 890 |
| 23 | $C_9H_4N_6OS_2$ | 39.39 | 1.70 | 29.80 | 3000 | 1695 | 1565 | 1530 | 1450 |
| | ¼$C_2H_5OH$ | 39.02 | 1.83 | 29.81 | 1410 | 1245 | 1230 | 970 | 720 |
| 24 | $C_9H_4N_6OS_2$ | 39.12 | 1.46 | 30.42 | 3060 | 1680 | 1570 | 1520 | 1470 |
| | | 39.52 | 2.09 | 30.23 | 1405 | 1235 | 1230 | 845 | 730 |
| 25 | $C_{10}H_6N_6OS_2$ | 41.37 | 2.08 | 28.95 | 3400 | 2760 | 1710 | 1560 | 1510 |
| | | 41.37 | 2.19 | 29.00 | 1480 | 1450 | 1410 | 1245 | 1170 |
| 26 | $C_{10}H_6N_6OS_2$ | 41.37 | 2.08 | 28.95 | 3150 | 3080 | 1690 | 1570 | 1530 |
| | | 41.49 | 2.50 | 28.71 | 1500 | 1440 | 1235 | 875 | 750 |
| 27 | $C_{11}H_8N_6OS_2$ | 43.41 | 2.65 | 27.62 | 3080 | 2920 | 1725 | 1650 | 1580 |
| | | 43.50 | 3.26 | 27.70 | 1525 | 1490 | 1475 | 1415 | 750 |
| 28 | $C_{13}H_{12}N_6OS_2$ | 46.97 | 3.64 | 25.29 | 2940 | 2850 | 1720 | 1670 | 1540 |
| | | 46.85 | 3.64 | 24.96 | 1520 | 1490 | 1430 | 1250 | 1160 |
| 29 | $C_{13}H_{12}N_6OS_2$ | 46.97 | 3.64 | 25.29 | 2950 | 2640 | 1740 | 1540 | 1270 |
| | | 47.46 | 3.98 | 25.55 | 1235 | 1205 | 1190 | 1170 | 750 |
| 30 | $C_{11}H_8N_6OS_2$ | 42.16 | 2.90 | 26.82 | 3480 | 2720 | 1720 | 1570 | 1510 |
| | ½$H_2O$ | 42.28 | 2.88 | 26.82 | 1475 | 1235 | 1170 | 980 | 590 |
| 31 | $C_{12}H_{10}N_6OS_2$ | 46.07 | 4.38 | 25.05 | 2920 | 1735 | 1650 | 1570 | 1535 |
| | $C_3H_7NO$ | 46.11 | 4.39 | 25.08 | 1510 | 1475 | 1440 | 1385 | 870 |
| 32 | $C_9H_3ClN_6OS_2$ | 37.55 | 3.00 | 25.54 | 2700 | 1730 | 1640 | 1580 | 1530 |
| | $C_3H_7NO$ | 37.84 | 2.83 | 25.46 | 1500 | 1475 | 1425 | 1385 | 1240 |
| 33 | $C_{12}H_8N_6OS_2$ | 45.56 | 2.55 | 26.57 | 3180 | 1710 | 1565 | 1530 | 1500 |
| | | 45.54 | 2.69 | 26.22 | 1475 | 1435 | 1415 | 1230 | 1160 |
| 34 | $C_{14}H_{13}N_5O_3S_2$ | 47.58 | 3.71 | 23.78 | 3170 | 3120 | 1695 | 1570 | 1540 |
| | ½$H_2O$ | 47.53 | 3.56 | 23.64 | 1505 | 1430 | 1245 | 1005 | 770 |
| 35 | $C_{13}H_{10}N_6OS_2$ | 47.42 | 3.39 | 24.58 | 3170 | 1710 | 1690 | 1560 | 1530 |
| | ¼$C_2H_5OH$ | 46.91 | 3.23 | 24.50 | 1510 | 1470 | 1440 | 1230 | 735 |
| 36 | $C_{14}H_{12}N_6OS_2$ | 48.84 | 3.82 | 24.14 | 3400 | 2910 | 1730 | 1640 | 1555 |
| | ¼$C_3H_7NO$ | 48.89 | 4.31 | 24.15 | 1515 | 1450 | 1380 | 1250 | 1205 |
| 37 | $C_{12}H_{11}N_7O_2S$ | 42.98 | 3.91 | 29.24 | 3100 | 2950 | 1730 | 1705 | 1570 |
| | $H_2O$ | 43.33 | 3.59 | 29.28 | 1550 | 1530 | 1450 | 1230 | 910 |
| 38 | $C_{14}H_8N_6O_2S$ | 51.59 | 3.21 | 25.23 | 3050 | 1730 | 1635 | 1555 | 1530 |
| | ¼$C_3H_7NO$ | 51.90 | 3.46 | 25.11 | 1510 | 1470 | 1450 | 1230 | 755 |
| 39 | $C_{14}H_{10}N_6O_2S$ | 51.52 | 3.09 | 25.76 | 3050 | 1735 | 1555 | 1530 | 1515 |
| | | 51.67 | 2.72 | 25.55 | 1470 | 1450 | 1270 | 1235 | 755 |
| 40 | $C_{14}H_{10}N_6O_2S$ | 51.30 | 3.75 | 25.09 | 1705 | 1560 | 1520 | 1260 | 1230 |
| | ¼$C_3H_7NO$ | 51.55 | 3.52 | 24.24 | 1150 | 1100 | 995 | 965 | 745 |
| 41 | $C_{13}H_8N_6O_3S$ | 47.73 | 3.18 | 24.96 | 3040 | 1700 | 1560 | 1530 | 1490 |
| | ¼$C_3H_7NO$ | 47.93 | 3.06 | 24.95 | 1270 | 1260 | 1240 | 1090 | 765 |
| 42 | $C_{12}H_8N_6OS$ | 50.69 | 2.84 | 29.56 | 3150 | 1705 | 1570 | 1530 | 1490 |
| | | 50.59 | 2.93 | 29.57 | 1150 | 970 | 770 | 695 | 610 |
| 43 | $C_{16}H_{16}N_6OS$ | 55.71 | 4.82 | 24.36 | 3155 | 2950 | 1720 | 1710 | 1625 |
| | ¼$H_2O$ | 55.92 | 4.73 | 24.25 | 1575 | 1530 | 1480 | 1130 | 770 |
| 44 | $C_{13}H_{10}N_6O_2S$ | 49.67 | 3.21 | 26.74 | 3150 | 1710 | 1570 | 1530 | 1510 |
| | | 49.74 | 3.34 | 26.63 | 1470 | 1250 | 1140 | 1020 | 970 |
| 45 | $C_{12}H_7FN_6OS$ | 47.68 | 2.33 | 27.80 | 3050 | 1705 | 1600 | 1570 | 1525 |
| | | 47.85 | 2.44 | 27.53 | 1500 | 1470 | 1230 | 1215 | 1110 |
| 46 | $C_{12}H_7ClN_6OS$ | 45.21 | 2.21 | 26.77 | 3140 | 1710 | 1570 | 1530 | 1490 |
| | | 45.29 | 2.37 | 26.44 | 1475 | 1150 | 970 | 770 | 610 |
| 47 | $C_{11}H_6N_6OS$ | 48.88 | 2.24 | 31.10 | 3060 | 3030 | 1690 | 1575 | 1520 |
| | | 48.79 | 2.55 | 30.79 | 1480 | 1440 | 1240 | 990 | 770 |
| 48 | $C_{14}H_{12}N_6OS$ | 53.83 | 3.87 | 26.91 | 3180 | 1700 | 1560 | 1515 | 1470 |
| | | 53.62 | 3.99 | 26.43 | 1450 | 1140 | 990 | 770 | 740 |
| 49 | $C_{14}H_{12}N_6OS$ | 53.83 | 3.87 | 26.91 | 3140 | 2900 | 1710 | 1570 | 1550 |
| | | 53.86 | 4.03 | 26.88 | 1530 | 1475 | 1210 | 970 | 770 |
| 50 | $C_{14}H_{12}N_6OS$ | 53.83 | 3.87 | 26.91 | 3210 | 1705 | 1560 | 1520 | 1470 |
| | | 53.76 | 4.18 | 26.57 | 1445 | 1230 | 1220 | 995 | 770 |
| 51 | $C_{14}H_{12}N_6O_2S$ | 51.21 | 3.68 | 25.59 | 3150 | 1710 | 1590 | 1570 | 1540 |
| | | 51.19 | 3.92 | 25.31 | 1525 | 1270 | 1250 | 1160 | 1030 |
| 52 | $C_{14}H_{12}N_6O_2S$ | 51.21 | 3.68 | 25.59 | 3150 | 1700 | 1560 | 1520 | 1500 |
| | | 51.25 | 3.76 | 25.48 | 1470 | 1260 | 1235 | 970 | 800 |
| 53 | $C_{13}H_9FN_6OS$ | 49.36 | 2.87 | 26.57 | 3160 | 1690 | 1550 | 1510 | 1490 |
| | | 49.30 | 3.06 | 26.63 | 1210 | 1045 | 990 | 810 | 750 |
| 54 | $C_{13}H_9ClN_6OS$ | 46.92 | 2.73 | 25.26 | 3060 | 1710 | 1570 | 1550 | 1530 |
| | | 46.93 | 2.87 | 25.30 | 1475 | 970 | 890 | 865 | 770 |
| 55 | $C_{13}H_9ClN_6OS$ | 46.92 | 2.73 | 25.26 | 3150 | 1700 | 1560 | 1520 | 1480 |
| | | 46.68 | 2.99 | 24.80 | 1210 | 1085 | 970 | 805 | 765 |

-continued

| Compound of Example | Formula | Elemental Analysis % (calc'd)/(found) | | | IR Absorption Spectrum (KBr) cm$^{-1}$ | | | | |
|---|---|---|---|---|---|---|---|---|---|
| | | C | H | N | | | | | |
| 56 | $C_{13}H_8Cl_2N_6OS$ | 42.52 | 2.20 | 22.89 | 3130 | 1700 | 1560 | 1520 | 1455 |
| | | 42.44 | 2.35 | 22.83 | 1210 | 1125 | 985 | 970 | 820 |
| 57 | $C_{19}H_{14}N_6OS$ | 58.15 | 4.11 | 21.42 | 3170 | 1715 | 1700 | 1555 | 1515 |
| | $H_2O$ | 58.66 | 3.89 | 21.05 | 1480 | 1465 | 740 | 690 | 590 |
| 58 | $C_{14}H_{12}N_6OS$ | 53.83 | 3.87 | 26.91 | 3150 | 1705 | 1570 | 1525 | 1490 |
| | | 53.88 | 3.96 | 26.54 | 1470 | 1135 | 980 | 765 | 695 |
| 59 | $C_{15}H_{14}N_6OS$ | 55.20 | 4.32 | 25.75 | 3150 | 2940 | 1710 | 1560 | 1515 |
| | | 55.56 | 4.38 | 25.89 | 1470 | 1430 | 1140 | 760 | 690 |
| 60 | $C_{14}H_{12}N_6OS$ | 53.83 | 3.87 | 26.91 | 3130 | 1710 | 1570 | 1525 | 1490 |
| | | 53.58 | 3.93 | 24.48 | 1470 | 1445 | 970 | 770 | 745 |
| 61 | $C_{15}H_{14}N_6OS$ | 55.20 | 4.32 | 25.75 | 3140 | 2920 | 1700 | 1560 | 1520 |
| | | 54.91 | 4.27 | 25.36 | 1485 | 1470 | 1445 | 770 | 745 |
| 62 | $C_{13}H_8N_6OS$ | 52.49 | 3.12 | 27.83 | 3400 | 3120 | 3060 | 1700 | 1610 |
| | $\frac{1}{4}C_3H_7NO$ | 52.57 | 3.49 | 27.25 | 1565 | 1520 | 1470 | 970 | 770 |
| 63 | $C_{19}H_{12}N_6OS$ | 60.54 | 3.34 | 22.30 | 3130 | 1715 | 1690 | 1540 | 1490 |
| | $\frac{1}{4}H_2O$ | 60.28 | 3.54 | 22.24 | 1435 | 1255 | 1190 | 1140 | 770 |
| 64 | $C_{12}H_8N_6O_2S$ | 48.07 | 3.09 | 27.48 | 3180 | 1710 | 1560 | 1530 | 1485 |
| | $\frac{1}{4}C_3H_7NO$ | 47.77 | 2.93 | 27.33 | 1245 | 1230 | 1210 | 1170 | 760 |
| 65 | $C_{16}H_{16}N_6O_2S$ | 53.92 | 4.53 | 23.58 | 2970 | 1720 | 1560 | 1530 | 1510 |
| | | 54.74 | 4.90 | 22.87 | 1250 | 1230 | 1185 | 1170 | 825 |
| 66 | $C_{12}H_7FN_6O_2S$ | 45.28 | 2.22 | 26.41 | 3200 | 1730 | 1565 | 1400 | 1250 |
| | | 45.45 | 2.42 | 26.57 | 1230 | 1205 | 1170 | 830 | 770 |
| 67 | $C_{12}H_7ClN_6O_2S$ | 43.05 | 2.11 | 25.11 | 3150 | 1710 | 1565 | 1530 | 1490 |
| | | 43.47 | 2.53 | 24.85 | 1240 | 1220 | 1170 | 1060 | 820 |
| 68 | $C_{16}H_{14}N_6O_2S$ | 54.22 | 3.98 | 23.72 | 3200 | 1725 | 1710 | 1575 | 1565 |
| | | 53.98 | 4.06 | 23.35 | 1550 | 1495 | 1260 | 1235 | 1170 |
| 69 | $C_{17}H_{18}N_6O_2S$ | 54.59 | 5.33 | 22.37 | 2960 | 1710 | 1580 | 1555 | 1530 |
| | $\frac{1}{4}C_3H_7NO$ | 54.15 | 4.94 | 22.45 | 1510 | 1245 | 1185 | 1155 | 775 |
| 70 | $C_{12}H_8N_6OS_2$ | 45.30 | 2.55 | 26.57 | 3130 | 1690 | 1550 | 1515 | 1465 |
| | | 45.63 | 2.60 | 26.41 | 1430 | 1225 | 1210 | 1000 | 760 |
| 71 | $C_{16}H_{16}N_6OS_2$ | 51.59 | 4.33 | 22.57 | 3150 | 2950 | 1720 | 1710 | 1565 |
| | | 51.58 | 4.26 | 23.04 | 1525 | 1480 | 1235 | 1105 | 825 |
| 72 | $C_{13}H_{10}N_6OS_2$ | 47.49 | 3.25 | 24.62 | 3400 | 3130 | 1700 | 1600 | 1560 |
| | $\frac{1}{4}C_2H_5OH$ | 47.50 | 3.31 | 24.54 | 1520 | 1470 | 1425 | 1225 | 730 |
| 73 | $C_{13}H_8ClN_5O_2S$ | 46.96 | 2.77 | 20.29 | 3080 | 1720 | 1710 | 1635 | 1590 |
| | $\frac{1}{4}C_2H_5OH$ | 47.22 | 2.55 | 20.20 | 1520 | 1490 | 1460 | 1280 | 1265 |
| 74 | $C_{10}H_5N_5O_2S$ | 46.52 | 2.45 | 26.50 | 1695 | 1575 | 1525 | 1485 | 1240 |
| | $\frac{1}{4}C_3H_7NO$ | 46.39 | 2.40 | 26.26 | 985 | 965 | 750 | 740 | 590 |
| 75 | $C_{10}H_5N_5OS_2$ | 43.97 | 2.28 | 24.42 | 3170 | 3080 | 1680 | 1570 | 1520 |
| | $\frac{1}{4}C_2H_5OH$ | 43.53 | 2.12 | 24.64 | 1465 | 1235 | 1140 | 765 | 730 |
| 76 | $C_{14}H_{11}N_5OS$ | 56.55 | 3.73 | 23.55 | 2730 | 1725 | 1570 | 1520 | 1460 |
| | | 56.64 | 3.93 | 23.28 | 1345 | 1330 | 1040 | 770 | 740 |
| 77 | $C_{14}H_{10}ClN_5OS$ | 50.68 | 3.04 | 21.11 | 3100 | 1685 | 1570 | 1520 | 1460 |
| | | 50.57 | 3.18 | 20.99 | 1420 | 1340 | 1320 | 1230 | 770 |
| 78 | $C_{13}H_9ClN_6OS$ | 46.92 | 2.72 | 25.26 | 3170 | 1700 | 1555 | 1520 | 1475 |
| | | 47.15 | 3.04 | 24.98 | 1445 | 1125 | 1035 | 770 | 740 |
| 79 | $C_{19}H_{22}N_6O_2S$ | 57.27 | 5.56 | 21.09 | 2950 | 1705 | 1575 | 1530 | 1480 |
| | | 57.16 | 5.57 | 21.11 | 1450 | 1265 | 1120 | 975 | 775 |
| 80 | $C_{12}H_8N_6OS$ | 47.68 | 3.33 | 27.80 | 3480 | 1720 | 1575 | 1530 | 1500 |
| | $H_2O$ | 47.79 | 3.45 | 27.85 | 1475 | 1230 | 985 | 745 | 600 |
| 81 | $C_{10}H_5N_7OS$ | 44.59 | 2.34 | 35.08 | 1730 | 1675 | 1600 | 1570 | 1545 |
| | $\frac{1}{4}H_2O$ | 44.46 | 2.24 | 35.32 | 1525 | 1480 | 1240 | 1170 | 745 |
| 82 | $C_{15}H_{14}N_6OS$ | 55.20 | 4.32 | 25.75 | 3100 | 2960 | 1735 | 1580 | 1525 |
| | | 55.13 | 4.29 | 26.03 | 1470 | 1240 | 990 | 750 | 630 |
| 83 | $C_{15}H_{12}N_6OS$ | 55.54 | 3.73 | 25.91 | 2930 | 1710 | 1560 | 1525 | 1480 |
| | | 55.70 | 3.94 | 25.50 | 1420 | 1240 | 1160 | 825 | 750 |
| 84 | $C_{14}H_9N_5OS$ | 56.94 | 3.07 | 23.71 | 3100 | 2880 | 1685 | 1670 | 1545 |
| | | 56.64 | 3.32 | 22.96 | 1310 | 1150 | 940 | 775 | 750 |
| 85 | $C_{19}H_{25}N_7O_4S$ | 49.99 | 5.74 | 21.48 | | | | | |
| | $\frac{1}{2}H_2O$ | 50.24 | 6.00 | 21.25 | | | | | |
| 86 | $C_{16}H_{19}N_7O_5S$ | 42.01 | 5.07 | 21.14 | | | | | |
| | $2H_2O$ | 42.01 | 4.64 | 21.97 | | | | | |
| 87 | $C_{13}H_9NaN_6OS$ | 46.15 | 3.28 | 24.84 | | | | | |
| | $H_2O$ | 45.86 | 3.40 | 24.80 | | | | | |
| 88 | $C_{13}H_9KN_6OS1.5H_2O$ | 42.96 | 3.33 | 23.13 | | | | | |
| | | 42.76 | 3.40 | 23.23 | | | | | |
| 89 | $C_{13}H_9LiN_6OS$ | 45.88 | 3.85 | 24.70 | | | | | |
| | $2H_2O$ | 45.58 | 3.80 | 24.55 | | | | | |

The pharmacological test examples and the anti-allergic activity of the compounds of this invention are described hereinafter in detail.

TEST EXAMPLE 1

(i) Preparation of Antiserum 1 mg of egg albumin dissolved in 0.2 ml of saline was intramuscularly administered to each of Sprague-Dawley male rats weighing 300 to 350 g (Charles River Japan Inc.), and then 1 ml of a suspension of sterilized Bordetella pertussis (2×10¹⁰ cells) in saline was administered intraperitoneally to the rats. After 14 days, blood was drawn from the rats to obtain an antiserum. The PCA titer of this serum was found to be about 1:64 to 128 when measured with the 48 hours PCA in rats.

(ii) Passive Peritoneal Anaphylaxis (PPA) Test

The test was conducted according to the method of Orange et al [Orange, R. P., Stechschulte, D. J., Austen, K. F., *J. Immunol.*, 105, pp1087–1095 (1970)]. Sprague-Dawley male rats weighing 250 to 400 g (5 rats per group) were passively sensitized by administering 5 ml of 5-fold dilution antiserum (prepared by diluting the above antiserum with saline). 2 hours later, 5 ml of an egg albumin solution prepared by dissolving 2 mg of egg albumin in phosphate buffered saline containing 0.9 mM of calcium chloride was administered intraperitoneally to the rats. After 5 minutes, the rats were sacrificed by decapitation, and peritoneal fluid was pooled and centrifuged at 300×G at 4° C. for 10 minutes. Then, amounts of SRS-A and histamine in the supernatant were determined.

The quantitative determination of SRS-A was carried out according to the method of Stechschulte et al [Stechschulte, D. J., Auste, K. F., Bloch, K. J., *J. Exp. Med.*, 125, pp127–147 (1967)] using a guinea pig ileum specimen in the presence of mepyramine and atropine. The amount of SRS-A was expressed in terms of unit, i.e., one unit of SRS-A activity was defined as the concentration required to produce a contraction of guinea pig ileum equal in amplitude to that produced by 5 ng of histamine, and the total released amount of SRS-A per rat (unit/rat) was calculated.

The quantitative determination of histamine was carried out according to the method of Shore et al [Shore, P. A., Bunkhalter, A. H., Cohn, V. H., *J. Pharmacol. Exp. Ther.*, 127, pp182–186 (1959)], and the total released amount of histamine per rat (μg/rat) was calculated.

In this test, the test compound of this invention was administered as follows. 2 mg of a test compound was dissolved in 10 ml of phosphate buffered saline containing 0.9 mM of calcium chloride, an equimolar amount of sodium hydroxide to test compound, 2% of dimethyl sulfoxide and 2% of ethanol, and the solution was administered intraperitoneally to the rats at a dose of 1 mg/kg 30 seconds before the injection of egg albumin for inducing PPA. For a control group, the same solution without test compound and sodium hydroxide was administered.

The inhibitory activity on release of histamine and SRS-A by the PPA reaction in the treated group was calculated by the following formula:

$$\text{Inhibition (\%)} = \frac{a - b}{a - c} \times 100$$

wherein:
a represents a mean value of released amount in the control group.
b represents a mean value of released amount in the treated group.
c represents a mean value of spontaneously released amount.

The inhibitory activities of the compounds of this invention determined by the above tests are shown in Table 1.

TABLE 1

| Compound of Example | Inhibition (%) Histamine | SRS-A |
|---|---|---|
| 1 | 83 | 64 |
| 2 | 85 | 52 |
| 3 | 93 | 42 |
| 8 | 83 | 37 |
| 9 | 80 | 50 |
| 11 | 89 | 66 |
| 12 | 87 | 52 |
| 17 | 82 | 55 |
| 23 | 84 | 51 |
| 27 | 81 | 63 |
| 32 | 87 | 63 |
| 33 | 82 | 70 |
| 35 | 88 | 45 |
| 36 | 83 | 41 |
| 41 | 91 | 62 |
| 42 | 99 | 54 |
| 43 | 75 | 59 |
| 44 | 81 | 70 |
| 57 | 86 | 61 |
| 62 | 94 | 55 |
| 66 | 89 | 47 |
| 80 | 91 | 42 |
| 82 | 82 | 52 |
| DSCG* | 93 | 0 |

*DSCG Sodium Cromoglycate (administered at 1 mg/kg of body weight)

TEST EXAMPLE 2

PCA Test

In this test, the antiserum described in Test Example 1 was used after it was diluted with saline so as to provide a blue spot having a diameter of about 10 mm in the following control group.

Sprague-Dowley male rats weighing about 180 g (5 rats per group) were sensitized by injecting 0.05 ml of the diluted antiserum into the shaved dorsal skin. 48 hours later, the animals were challenged with 1 ml of saline containing 5 mg of egg albumin and 5 mg of Evans blue dye administered via a tail vein. 30 minutes later, the rats were sacrificed by decapitation. The dorsal skin was removed, and the long and short axis of the each wheal was measured.

In this test, the test compound was administered as follows. 20 mg of a test compound was suspended in a 0.5% CMC aqueous solution, and the suspension was administered to each of the rats in an amount of 20 mg/kg 30 minutes before the antigen challenge. For a control group, only a 0.5% CMC solution was administered.

The inhibitory activity on the PCA reaction in the treated group was calculated by the following formula:

$$\text{Inhibition (\%)} = \frac{a - b}{a} \times 100$$

wherein:
a represents a mean value of blue spot area in the control group.
b represents a mean value of blue spot area in the treated group.

The inhibitory activity of the compounds of this invention determined by the above test are shown in Table 2.

TABLE 2

| Compound of Example | Inhibition (%) |
|---|---|
| 1 | 46 |
| 6 | 36 |
| 7 | 40 |
| 9 | 52 |
| 11 | 32 |
| 12 | 36 |
| 13 | 34 |
| 17 | 50 |
| 21 | 35 |
| 23 | 31 |
| 24 | 45 |
| 28 | 34 |
| 29 | 39 |
| 31 | 32 |
| 32 | 35 |
| 33 | 47 |
| 35 | 45 |
| 36 | 40 |
| 39 | 38 |
| 42 | 48 |
| 45 | 57 |
| 47 | 38 |
| 64 | 33 |
| 69 | 34 |
| 73 | 48 |
| 75 | 32 |
| 80 | 31 |
| 83 | 44 |
| DSCG* | 8 |

*DSCG Sodium Cromoglycate (administered at 100 mg/kg of body weight)

Example of preparations containing the compound of this invention are described hereinafter.

PREPARATION EXAMPLE 1

Tablets each containing 50 mg of the compound of the present invention are prepared from the following formulation.

| | | |
|---|---|---|
| Compound of Present Invention* | | 50 mg |
| Lactose | | 35 mg |
| Starch | | 24.5 mg |
| Magnesium Stearate | | 0.5 mg |
| | Total | 110 mg per tablet |

PREPARATION EXAMPLE 2

A syrup preparation containing 10 mg of the compound of the present invention per ml was prepared from the following formulation.

| | | |
|---|---|---|
| Compound of Present Invention* | | 1000 mg |
| Polysolbate 80 | | 1000 mg |
| Syrup | | quantum sufficient |
| | Total | 100 ml |

*6-(2-Phenylethyl)-[1,3,4]thiadiazolo[3,2-a][1,2,3]-triazolo[4,5-d]pyrimidin-9(1H)-one While the invention has been described in detail and with reference to specific embodiments thereof, it will be apparent to one skilled in the art that various changes and modifications can be made therein without departing from the spirit and scope thereof.

What is claimed is:

1. A compound represented by the formula (I)

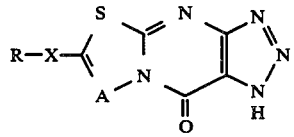

wherein:

A represents CH or N;

R represents a phenyl group, biphenyl group, naphthyl group, furyl group, thienyl group, pyridyl, isochromanyl, chromanyl, chromenyl, benzodioxanyl group, thiazolyl group, isothiazolyl group, thiadiazolyl group, imidazolyl group, pyrazolyl group, triazolyl group, pyrimidinyl group, morpholinyl group, pyrazinyl group, pyridazinyl group, pyrrolidinyl group, piperidinyl group, piperazinyl group, homopiperazinyl group, pyrrolyl group, pyrrolinyl group, imidazolyl group, imidazolidinyl group, oxazolinyl group, oxazoldinyl group, tetrazolyl group, thiazolidinyl group, indolyl group, quinolyl group, naphthyridinyl group, quinazolinyl group, pteridinyl group, isobenzofuranyl group, carbazolyl group, acridinyl group, xanthenyl group, phenoxazinyl or perimidinyl group, each of which may be substituted with one or more substituents selected from the group consisting of an alkyl group having 1 to 6 carbon atoms, an alkylene group having 1 to 10 carbon atoms, a cycloalkyl group having 3 to 10 carbon atoms, an alkoxy group having 1 to 6 carbon atoms, an alkylenedioxy group having 1 to 8 carbon atoms and a halogen atom; and X represents a single bond, an alkylene group having 1 to 10 carbon atoms or an alkenylene group having 2 to 10 carbon atoms, each of which may be bonded to the substituent R or the condensed ring via an oxygen atom or a sulfur atom and may be substituted with one or more substituents selected from the group consisting of an alkyl group having 1 to 6 carbon atoms, a phenyl group, biphenyl group, naphthyl group, furyl group, thienyl group, pyridyl, isochromanyl, chromanyl, chromenyl, benzodioxanyl group, thiazolyl group, isothiazolyl group, thiadiazolyl group, imidazolyl group, pyrazolyl group, triazolyl group, pyrimidinyl group, morpholinyl group, pyrazinyl group, pyridazinyl group, pyrrolidinyl group, piperidinyl group, piperazinyl group, homopiperazinyl group, pyrrolyl group, pyrrolinyl group, imidazolyl group, imidazolidinyl group, oxazolinyl group, oxazoldinyl group, tetrazolyl group, thiazolidinyl group, indolyl group, quinolyl group, naphthyridinyl group, quinazolinyl group, pteridinyl group, isobenzofuranyl group, carbazolyl group, acridinyl group, xanthenyl group, phenoxazinyl or perimidinyl group; and physiologically acceptable salts thereof.

2. A compound or a salt thereof according to claim 1, wherein X represents an alkylene group and R represents a phenyl group which may be substituted with one or more substituents selected from the group consisting of an alkyl group, an alkoxy group and a halogen atom.

3. A compound or a salt thereof according to claim 1, wherein X represents an ethylene group and R represents a phenyl group, an alkylphenyl group or a halophenyl group.

4. 6-(2-phenylethyl)-[1,3,4]thiadiazolo[3,2-a][1,2,3]triazolo[4,5-d]pyrimidin-9(1H)-one or a salt thereof according to claim 1.

5. 6-[2-(3-chlorophenyl)ethyl]-[1,3,4]thiadiazolo[3,2-a][1,2,3]triazolo[4,5-d]pyrimidin-9(1H)-one or a salt thereof according to claim 1.

6. 6-[2-(3,4-dichlorophenyl)ethyl]-[1,3,4]thiadiazolo[3,2-a][1,2,3]triazolo[4,5-d]pyrimidin-9(1H)-one or a salt thereof according to claim 1.

7. 6-[2-(2-chlorophenyl)ethyl]-[1,3,4]thiadiazolo[3,2-a][1,2,3]triazolo[4,5-d]pyrimidin-9(1H)-one or a salt thereof according to claim 1.

8. 6-[2-(2-methylphenyl)ethyl]-[1,3,4]thiadiazolo[3,2-a][1,2,3]triazolo[4,5-d]pyrimidin-9(1H)-one or a salt thereof according to claim 1.

* * * * *